United States Patent [19]

Sustek, Jr. et al.

[11] 4,193,290
[45] Mar. 18, 1980

[54] STEAM QUALITY ACOUSTIC MONITORING SYSTEM AND METHOD

[75] Inventors: Alvin J. Sustek, Jr.; Thomas G. Scott, both of Houston, Tex.

[73] Assignee: Texaco Inc., White Plains, N.Y.

[21] Appl. No.: 925,134

[22] Filed: Jul. 17, 1978

[51] Int. Cl.² ............................................. G01N 29/02
[52] U.S. Cl. ......................................................... 73/29
[58] Field of Search ...................... 73/29, 24, 592, 591

[56] References Cited

U.S. PATENT DOCUMENTS

| | | | |
|---|---|---|---|
| 2,788,656 | 4/1957 | Sander | 73/24 |
| 3,192,516 | 6/1965 | Simpkins et al. | 73/592 |
| 3,413,838 | 12/1968 | Duddy | 73/29 |
| 3,592,967 | 7/1971 | Harris | 73/592 |
| 3,673,857 | 7/1972 | Teitelbaum | 73/592 |

Primary Examiner—Anthony V. Ciarlante
Attorney, Agent, or Firm—Thomas H. Whaley; Carl G. Ries; Henry C. Dearborn

[57] ABSTRACT

Continuous steam quality monitoring is obtained by bleeding the steam through an orifice to generate acoustic energy. An acoustic transducer is coupled to the wall that contains the orifice. And, an amplifier with a narrow band acoustic frequency filter is employed so as to produce an output signal having an amplitude that is proportional to the quality of the steam.

6 Claims, 3 Drawing Figures

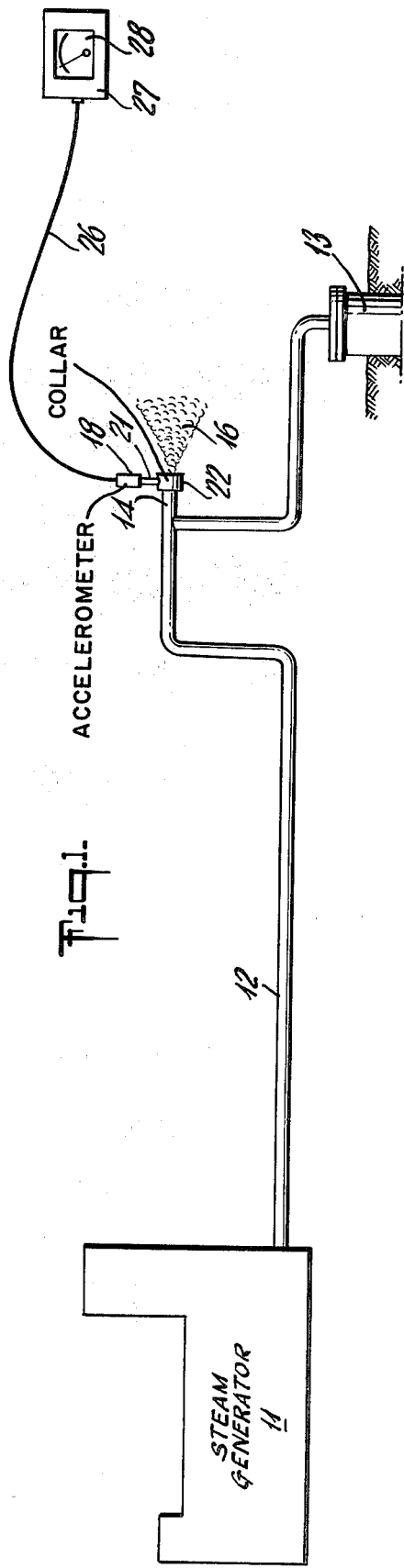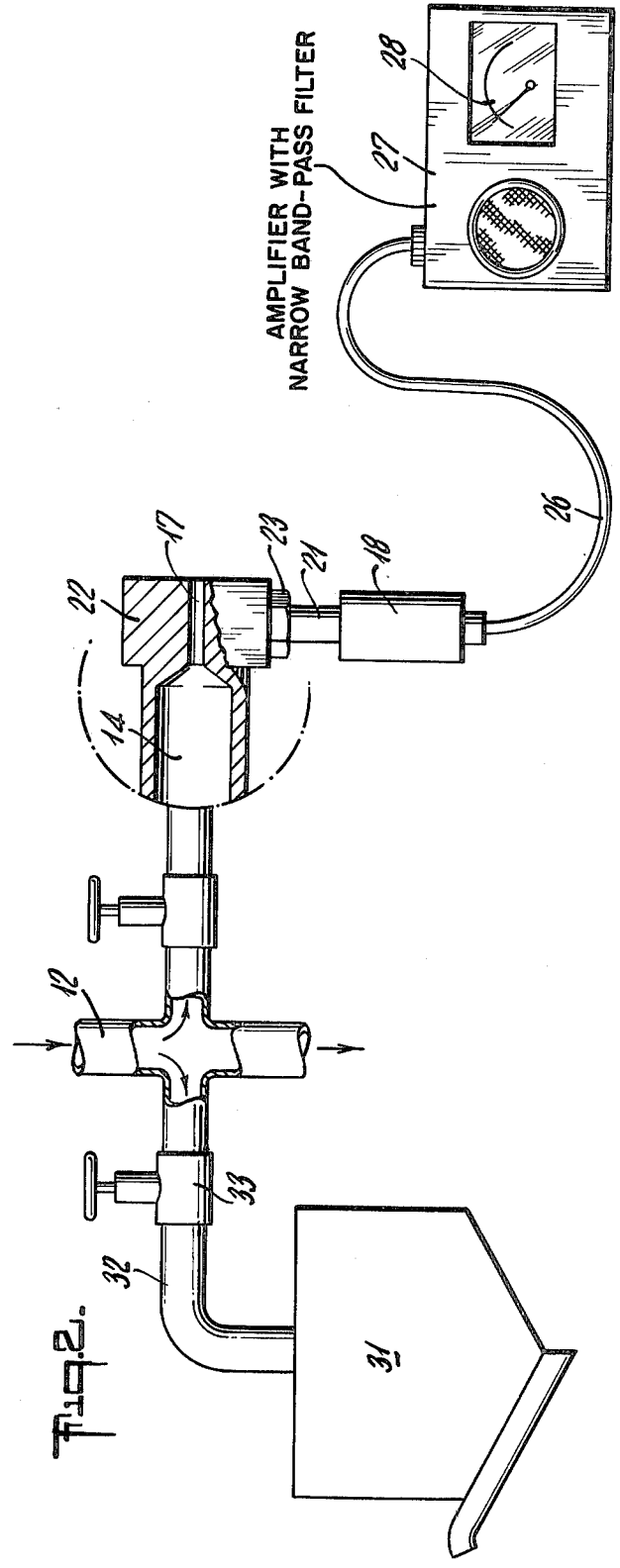

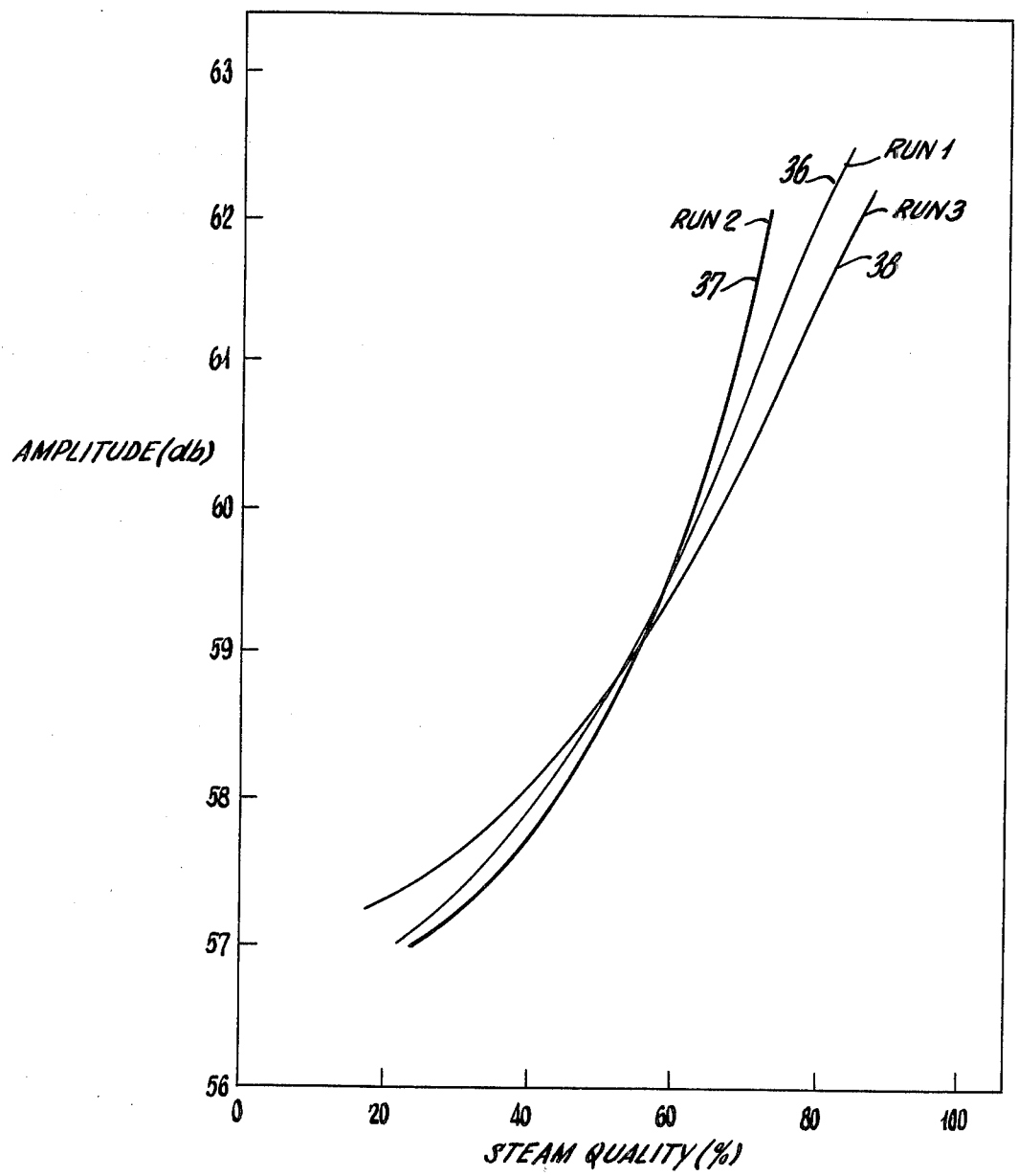

STEAM QUALITY ACOUSTIC MONITORING SYSTEM AND METHOD

BACKGROUND OF THE INVENTION

1. Field of the Invention

This invention concerns a system and method for measuring steam quality. It is particularly applicable to steam that is being injected into wells such as is done for stimulating production of petroleum.

2. Description of the Prior Art

Heretofore, there have been proposals for measuring the density of a gas which proposals were broadly applicable to a measurement of steam quality. However, such systems did not contemplate the use of steam as the gas to be measured. And, in addition, all of the known prior systems made use of a resonant chamber or a resonant arrangement, which would determine a relationship between the resonance in a given gas chamber and the density of the gas which had sound waves generated therein. Examples of such known prior arrangements are the following U.S. Pat. Nos.: Rubin 1,570,781, issued Jan. 26, 1926; Mikelson 2,283,750, issued May 19, 1942; F. M. Poole et al, 2,785,567, issued Mar. 19, 1957; and, Bourquard 3,346,065, issued Oct. 10, 1967.

On the other hand, this invention provides for a relatively simple system for measuring the quality of steam. It employs a determination of the amplitude of an acoustic signal (filtered at a particular frequency) as the steam flows through an orifice.

SUMMARY OF THE INVENTION

Briefly, the invention concerns a steam quality monitoring system for use with steam injection wells or the like. It comprises a conduit for delivering steam to be utilized, and an orifice connected to said conduit for permitting said steam to escape therethrough. It also comprises a sound transducer physically coupled adjacent to said orifice for generating sonic range frequency signals in accordance with sonic vibrations created by said steam flow through said orifice, and means for measuring the amplitude of said sonic signals at a predetermined frequency thereof to indicate the quality of said steam.

Again briefly, the invention concerns a steam quality monitoring system for use with steam injection wells or the like. It comprises a conduit for delivering steam for said injection, and an orifice in a wall of a chamber connected to said conduit for permitting said steam to escape therethrough. The said orifice has a diameter of about 0.015 inch. The system also comprises an acoustic accelerometer, and metallic means for directly coupling said accelerometer to said chamber wall adjacent to said orifice. It also comprises a narrow band-pass electrical filter connected to said accelerometer and having a central frequency of about 5,000 Hertz, and an electronic amplifier connected to the output of said filter. It also comprises means for measuring the amplitude of the output of said amplifier to indicate the quality of said steam.

Once more briefly, the invention concerns a method of continuously monitoring the quality of steam supplied to an injection well or the like. It comprises the steps of bleeding said steam through an orifice located adjacent to said injection well, and measuring the amplitude of acoustic energy generated by said orifice steam flow at a predetermined acoustic frequency. It also comprises the steps of calibrating said amplitude measurement in terms of quality of said steam.

BRIEF DESCRIPTION OF THE DRAWINGS

The foregoing and other objects and benefits of the invention will be more fully set forth below in connection with the best mode contemplated by the inventors of carrying out the invention, and in connection with which there are illustrations provided in the drawings, wherein:

FIG. 1 is a schematic illustration indicating a system for delivering steam to an injection well, with a monitor according to the invention connected thereto;

FIG. 2 is a schematic showing partly broken away in cross-section with some enlargement, illustrating the elements of a steam quality monitoring system according to the invention; and FIG. 3 is a graph illustrating the relationship of steam quality to the amplitude, in decibels, of an amplifier with filter in accordance with the invention.

DESCRIPTION OF THE PREFERRED EMOBDIMENTS

Determination of the quality of steam is an important aspect of steam injection in secondary recovery operations for petroleum oil wells, and the like. However, the practice of determining steam quality has heretofore employed devices and procedures that involved calculations and resulted in a time lag between the time when preliminary data was taken and a value for steam quality was obtained.

The steam quality of concern is the degree of dryness of the steam. This may be defined as the mass fraction of dry saturated steam relative to the steam mixture, at the measuring point. It is an important parameter in determining the efficiency of the steam generator. Also of greater importance is the effectiveness of a steam flood in a steam injection operation, i.e., where the steam is being injected into a well for treating the hydrocarbons in a formation downhole.

In order to continuously monitor the quality of steam being supplied to an injection well, and to do so adjacent to the well itself, a system according to this invention may be employed. Such a system is schematically illustrated in FIG. 1. Thus, there is a conventional steam generator 11 from which a steam line or pipe 12 goes for connection to an injection well 13. The pipe or conduit 12 includes a short section or chamber 14 at a convenient location adjacent to the well 13. The chamber 14 has an orifice 17 (See FIG. 2) that connects the chamber section 14 of the pipe or conduit 12 with the atmosphere. This orifice 17 acts to bleed some steam 16 (FIG. 1) from the conduit 12 off into the atmosphere at a location adjacent to the well 13. And, this steam jet will generate sonic range frequency signals.

It has been discovered that the sonic signals generated by the steam escaping through an orifice, such as the orifice 17 illustrated, may be monitored at a predetermined sonic frequency and will produce a variable amplitude of sound energy at that predetermined sonic frequency. Furthermore, such amplitude varies directly in accordance with the quality of steam.

In order to make such a determination, there is an acoustic accelerometer 18 that is directly coupled to the wall of the chamber 14 which contains the orifice 17. This coupling is such that it has a low attenuation of acoustic energy in transmitting the vibrations created by the steam escaping through the orifice 17. Therefore the acoustic energies i.e. vibrations, directly actuate the accelerometer 18.

Because of the temperatures involved with steam, it is preferable to employ a standoff connection between the accelerometer 18 and the wall that contains the orifice 17. Thus, as indicated in FIG. 2, such a standoff may comprise a metallic connecting rod 21 that is firmly attached to a collar 22 that forms the wall of the chamber 14, which contains the orifice 17. Such connection may be made in any feasible manner, e.g. by having a clamping nut 23 which is part of a conventional type clamping arrangement. For example, the rod 21 may have a flange (not shown) thereon which fits under the nut 23.

The accelerometer 18 generates electrical signals in accordance with the sound waves produced by the steam jet 16, and these are transmitted via an electrical circuit connector 26 to a unit 27. The unit 27 contains an electronic amplifier (not shown) along with a narrow band-pass electrical filer (not shown) that is adjusted or set at a predetermined frequency in the acoustic range.

It has been found that 5,000 cycles per second is a satisfactory frequency for setting the narrow band-pass filter. And, it has been discovered that the amplitude of acoustic energy at this frequency varies in accordance with the steam quality. Consequently, an amplitude meter 28 may be calibrated in terms of the quality of the steam that is flowing through the orifice 17.

FIG. 2 illustrates an arrangement for carrying out a calibration of the amplitude readings that are obtained by the meter 28 of the unit 27. There is a liquid-vapor separator 31 that is connected to the pipe 12 via a connecting pipe or conduit 32 which includes a valve 33. The separator 31 is schematically indicated. It may be like the separator shown and described in U.S. Pat. No. 3,499,488 which is assigned to the same assignee as this invention. Such a separator is used to make steam quality determinations by sampling the steam so that for each batch sampled and measured the corresponding reading of the meter 28 may be calibrated. It will be understood that details of the separator 31 and the steam quality measurements made thereby are not part, per se, of this invention.

FIG. 3 illustrates the result of three runs which were made to determine steam quality in relation to the amplitude of a particular sonic frequency signal. It will be observed that the FIG. 3 graph is laid out with the ordinate or vertical axis 34 representing the amplitude in decibels. Similarly, the steam quality is shown in percent along the abscissa of the graph. It will be observed that three curves 36, 37, and 38 represent three different runs indicated by "Run 1", "Run 2", and "Run 3", respectively. These runs were all made with the steam at 1,480 kPa and flowing at 1.8 cubic centimeters per second. It will be observed that there is a direct relationship between the amplitude (in decibels) of the output signals, and the steam quality (in percent).

It will be understood from the foregoing that a method in accordance with this invention is one for continuously monitoring the quality of steam that is supplied to an injection well or the like. It includes the step of bleeding the steam through an orifice that is located adjacent to the said injection well. This step is carried out in any feasible manner such as that illustrated. Thus, there is an orifice that is about 0.015 inch in diameter through which the steam escapes. This orifice is, of course, located through a wall of a chamber, e.g. the chamber 14, in the conduit 12 which is carrying the steam to the well.

Another step in the method is that of measuring the amplitude of acoustic energy generated by the steam flowing through the orifice. Such amplitude measurement is made at a predetermined acoustic frequency. This is carried out by having conventional amplification with electrical filter elements connected so as to provide a narrow band-pass filter. The band-pass is set for about 5,000 cycles Hertz with about a 1/10 octave band width. Then, the amplitude of the signals at the output of that filter are determined by any feasible electrical meter.

Finally, the calibration of the output amplitude (as measured by the foregoing meter) will be carried out so as to have the results determined in terms of the quality of the steam passing through the orifice. As indicated above in re FIG. 2, the calibration may include any feasible arrangement. It preferably makes use of a steam separator with accompanying equipment, for determining the steam quality in a batch type determination.

While particular embodiments of the invention have been described above in considerable detail, in accordance with the applicable statutes, this is not to be taken as in any way limiting the invention but merely as being descriptive thereof.

We claim:

1. Steam quality monitoring system for use with steam injection wells or the like, comprising
   a conduit for delivering steam to be utilized,
   an orifice connected to said conduit for permitting said steam to escape therethrough,
   a sound transducer physically coupled adjacent to said orifice for generating sonic range frequency signals in accordance with sonic vibrations created by said steam flow through said orifice, and
   means indicating the quality of said steam in response to the amplitude of said sonic signals at a predetermined frequency.

2. Steam quality monitoring system according to claim 1, wherein
   said sound transducer comprises an accelerometer.

3. Steam quality monitoring system according to claim 2, wherein
   said amplitude measuring means comprises an electronic amplifier with a narrow band-pass filter at said predetermined frequency.

4. Steam quality monitoring system for use with steam injection wells or the like, comprising
   a conduit for delivering steam for said injection,
   an orifice in a wall of a chamber connected to said conduit for permitting said steam to escape therethrough,
   said orifice having a diameter of about 0.015 inch,
   an acoustic accelerometer,
   metallic means for directly coupling said accelerometer to said chamber wall adjacent to said orifice,
   a narrow band-pass electrical filter connected to said accelerometer and having a central frequency of about five thousand Hertz,
   an electronic amplifier connected to the output of said filter, and
   means indicating the quality of said steam in response to the amplitude of the output of said amplifier.

5. Method of continuously monitoring the quality of steam supplied to an injection well or the like, comprising bleeding said steam through an orifice located adjacent to said injection well, measuring the amplitude of acoustic energy generated by said orifice steam flow at a predetermined acoustic frequency, and calibrating said amplitude measurement in terms of qualtiy of said steam.

6. Method according to claim 5, wherein said orifice is about 0.015 inch, and said predetermined frequency is about five kilo Hertz.

* * * * *